United States Patent [19]

Goode et al.

[11] Patent Number: 5,507,751
[45] Date of Patent: Apr. 16, 1996

[54] LOCALLY FLEXIBLE DILATOR SHEATH

[75] Inventors: Louis Goode, Evans City; Chun K. Lui, Monroeville, both of Pa.

[73] Assignee: Cook Pacemaker Corporation, Leechburg, Pa.

[21] Appl. No.: 255,602

[22] Filed: Jun. 8, 1994

Related U.S. Application Data

[60] Continuation-in-part of Ser. No. 42,375, Apr. 2, 1993, which is a division of Ser. No. 691,706, Apr. 26, 1991, Pat. No. 5,207,683, which is a continuation-in-part of Ser. No. 363,960, Jun. 9, 1989, Pat. No. 4,943,289, which is a continuation-in-part of Ser. No. 347,217, May 3, 1989, Pat. No. 5,011,482, which is a continuation-in-part of Ser. No. 298,100, Jan. 17, 1989, Pat. No. 5,013,310, which is a continuation-in-part of Ser. No. 269,771, Nov. 9, 1988, Pat. No. 4,988,347.

[51] Int. Cl.$^6$ ..................................................... A61B 17/50
[52] U.S. Cl. .......................... 606/108; 604/264; 606/170
[58] Field of Search ................................. 607/1, 2, 126; 606/108, 167, 170, 180, 184, 185, 159; 604/158, 164, 264

[56] References Cited

U.S. PATENT DOCUMENTS 3,118,159 1/1964 Kollmann ............................... 15/104.33

(List continued on next page.)

FOREIGN PATENT DOCUMENTS

| | | | |
|---|---|---|---|
| 2558376 | 7/1985 | France | 128/785 |
| 3532653 | 3/1987 | Germany | 128/344 |
| 3937594 | 5/1991 | Germany | |
| 4020155 | 1/1992 | Germany | |
| 8807390 | 10/1988 | Japan | 128/785 |
| 1277107 | 6/1972 | United Kingdom | 128/785 |

OTHER PUBLICATIONS

"Pacemaker Electrode Explantation Set," William Cook Europe A/S, Date Unknown.

Meibom, "A New Method for Transvenous Lead Explantation," 3rd European Symposium on Cardiac Pacing, Torremolinos, Malaga, Spain, PACE, vol. 8, May–Jun. 1985, Part II, Abstract 215, p. A–54.

Meibom, "A New Method for Transvenous Lead Explantation," Publisher (if any) and date of Publication Presently Unknown.

Meibom et al., "A New Method for Removal of Embedded Endocardial Electrodes," First Asian–Pacific Symposium, PACE, vol. 3, May–Jun. 1980, Abstract No. 77, p. 380.

(List continued on next page.)

*Primary Examiner*—William E. Kamm
*Assistant Examiner*—Kennedy J. Schaetzle
*Attorney, Agent, or Firm*—Richard J. Godlewski

[57] ABSTRACT

A locally flexible dilator sheath (10) for separating encapsulating tissue from an implanted cardiac electrical lead. The dilator sheath includes an elongated tubular member (11) of a rigid stainless steel material, which is sized for placement of the tubular member over a cardiac lead that is implanted in the vascular system of a patient. The distal end (13) of the rigid tubular member is beveled to ease the separation of extremely tough tissue that encapsulates an implanted cardiac lead. To ease insertion around curves in the vascular system of the patient, the elongated tubular member includes a relieved portion (14). The relieved portion includes a relief pattern (15) of apertures (16,17,19,23) in the elongated tubular member. The relief apertures preferably include diametrically opposed slots (24,25) that extend perpendicularly into the tubular member. Adjacent pairs (44,45) of slots are circumferentially offset a 90° angle (26) to add further lateral flexibility to the relieved portion. A polyester shrink tube (41) surrounds the relief apertures to provide integrity to the tubular member should the tubular member fracture when separating encapsulating tissue from the implanted lead.

20 Claims, 4 Drawing Sheets

U.S. PATENT DOCUMENTS

| | | | |
|---|---|---|---|
| 3,243,755 | 3/1966 | Johnston | 128/841 |
| 3,516,412 | 6/1970 | Ackerman | 128/419 P |
| 3,757,375 | 9/1973 | Strom | 15/104.33 |
| 3,841,308 | 10/1974 | Tate | 128/772 |
| 3,906,938 | 9/1975 | Fleischhacker | 128/772 |
| 4,000,745 | 1/1977 | Goldberg | 128/419 P |
| 4,011,869 | 3/1977 | Seiler, Jr. | 604/22 |
| 4,040,413 | 8/1977 | Ohshiro | 128/6 |
| 4,466,690 | 8/1984 | Osypka | 128/419 P |
| 4,471,777 | 9/1984 | McCorkle, Jr. | 128/303 R |
| 4,493,329 | 1/1985 | Crawford et al. | |
| 4,498,482 | 2/1985 | Williams | 128/786 |
| 4,541,681 | 9/1985 | Dorman et al. | 339/100 |
| 4,574,800 | 3/1986 | Peers-Trevarton | 128/785 |
| 4,576,162 | 3/1986 | McCorkle | 128/303 R |
| 4,582,056 | 4/1986 | McCorkle | 128/303 R |
| 4,621,636 | 11/1986 | Fogarty | |
| 4,706,671 | 11/1987 | Weinrib | 128/341 |
| 4,732,154 | 3/1988 | Shiber | 606/108 |
| 4,762,128 | 8/1988 | Rosenbluth | 604/96 |
| 4,762,130 | 8/1988 | Fogarty et al. | 604/96 |
| 4,773,432 | 9/1988 | Rydell | 128/772 |
| 4,791,939 | 12/1988 | Maillard | 128/419 P |
| 4,796,642 | 1/1989 | Harris | 128/772 |
| 4,834,090 | 5/1989 | Moore | 128/303 R |
| 4,848,342 | 7/1989 | Kaltenbach | 604/104 |
| 4,886,496 | 12/1989 | Conoscenti et al. | 604/96 |
| 4,886,500 | 12/1989 | Lazarus | 128/772 |
| 5,061,257 | 10/1991 | Martinez et al. | 604/282 |
| 5,067,489 | 11/1991 | Lind | 128/772 |
| 5,098,374 | 3/1992 | Othel-Jacobsen et al. | 606/108 |
| 5,108,368 | 4/1992 | Hammerslag et al. | 128/772 |
| 5,112,299 | 5/1992 | Pascaloff | 606/180 |
| 5,190,528 | 3/1993 | Fonger et al. | 604/171 |
| 5,329,923 | 7/1994 | Lundquist | 607/122 |
| 5,346,497 | 9/1994 | Simon et al. | 606/167 |

OTHER PUBLICATIONS

"Dotter Intravascular Retriever Set and Components," *Cook® Diagnostic and Interventional Products for Radiology, Cardiology and Surgery, Intravascular Retrieval*, 1986, p. 3.

"Wilson–Cook Grasping Forceps," *Wilson–Cook Medical, Inc., Products for Gastroenterology, Endoscopy and Surgery*, 1986–87 Catalog, p. 41.

"Loop Retrievers," *Cook Urological®, Urological Surgical Products, Stone Extractors and Retrievers*, 1986, p. 9.

"Boren–McKinney Retriever Set," *Cook Urological®, Urological Surgical Products, Stone Extractors and Retrievers*, 1986, p. 9.

"Curry Intravascular Retriever Sets and Components," *Cook® Diagnostic and Interventional Products for Radiology, Cardiology and Surgery, Intravascular Retrieval*, 1986, p. 2.

"Grasping Forceps," *Cook Urological®, Urological Surgical Products, Stone Extractors and Retrievers*, 1986, p. 8.

Alt et al., "Entfernung von drei infizierten Elektroden mit Hilfe eines neuen Extraktionsstiletts: Ein Fallbericht," *Herzschr Elektrophys*, vol. 2, 1991, pp. 29–34.

Alt et al., "Removal of Three Implanted Pacing Leads by Means of a New Extraction Stylet," translation of German reference *Herzschr Elektrophys*, vol. 2, 1991, pp., 29–34.

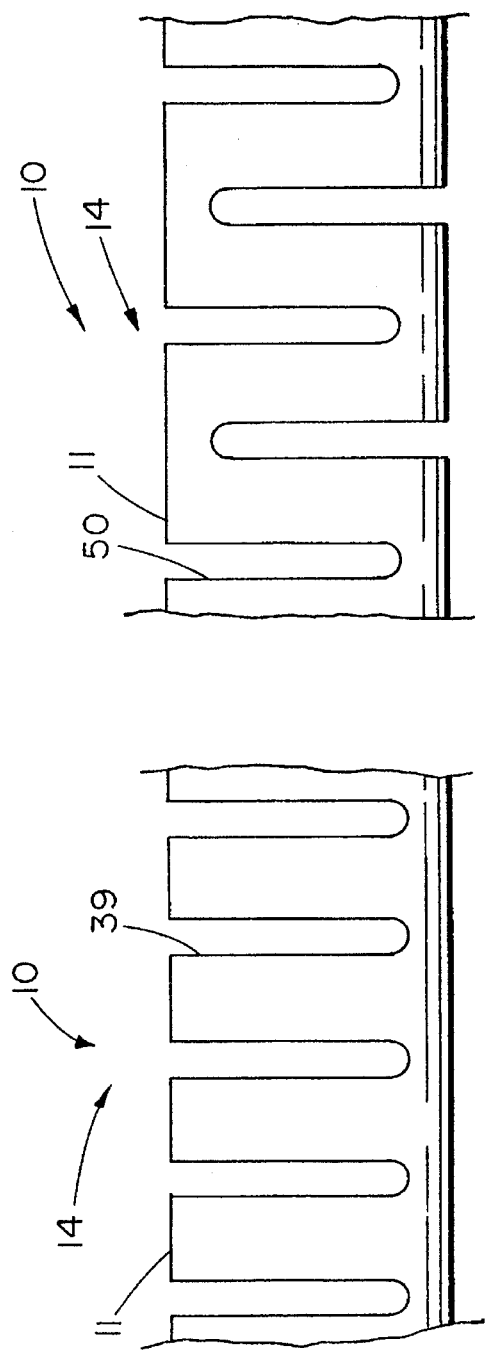
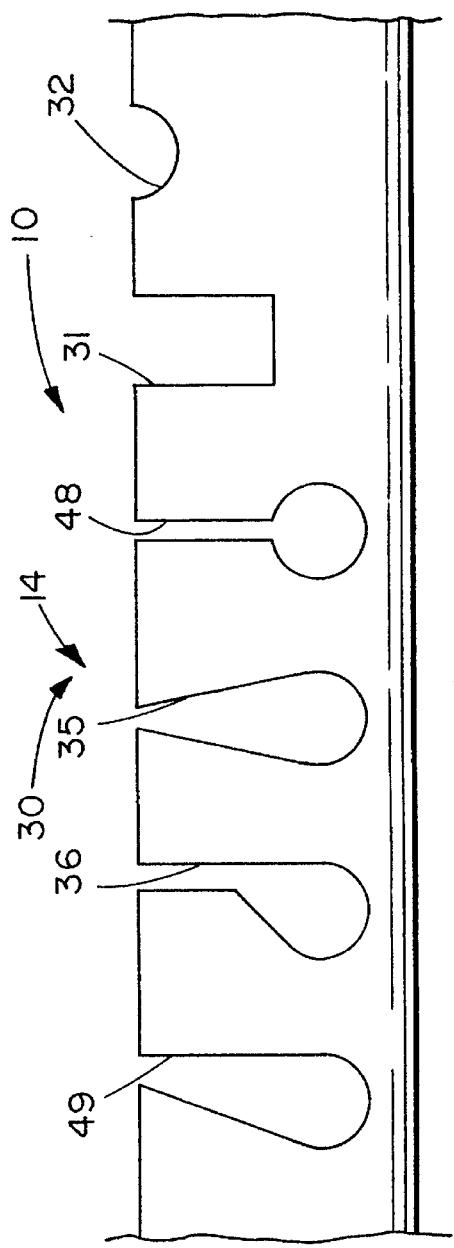

LOCALLY FLEXIBLE DILATOR SHEATH

CROSS-REFERENCE TO RELATED APPLICATIONS

This application is a continuation-in-part of pending application Ser. No. 08/042,375, filed Apr. 2, 1993, entitled "Apparatus for Removing an Elongated Structure Implanted in Biological Tissue," which is a divisional of application Ser. No. 07/691,706, filed Apr. 26, 1991, now U.S. Pat. No. 5,207,683, entitled "Apparatus for Removing an Elongated Structure Implanted in Biological Tissue," which is a continuation-in-part of application Ser. No. 07/363,960, filed Jun. 9, 1989, now U.S. Pat. No. 4,943,289, entitled "Apparatus for Removing an Elongated Structure Implanted in Biological Tissue," which is a continuation-in-part of application Ser. No. 07/347,217, filed May 3, 1989, now U.S. Pat. No. 5,011,482, entitled "Apparatus for Removing an Elongated Structure in Biological Tissue," which is a continuation-in-part of application Ser. No. 07/298,100, filed Jan. 17, 1989, now U.S. Pat. No. 5,013,310, entitled "Method and Apparatus for Removing an Implanted Pacemaker Lead," which is a continuation-in-part of application Ser. No. 07/269,771, filed Nov. 9, 1988, now U.S. Pat. No. 4,988,347, entitled "Method and Apparatus for Separating a Coiled Structure from Biological Tissue." All of the aforementioned pending applications and issued patents are incorporated herein by reference.

TECHNICAL FIELD

This invention relates generally to medical instruments and, in particular, to a locally flexible dilator sheath for separating encapsulating tissue from an implanted cardiac electrical lead.

BACKGROUND OF THE INVENTION

A pacemaker lead extends from the subcutaneous tissue pocket where a pacemaker is positioned through a vein and into a chamber of the heart. Similarly, defibrillator leads are affixed to the heart both internally and externally. Over time, the lead becomes encapsulated by fibrotic tissue against the wall of the vein or surrounding tissue. The tough, fibrotic tissue makes it difficult to remove a lead from the vein. Furthermore, removing a lead from this fibrotic tissue presents the risk of complications such as injury to the vein and bleeding. To avoid complications, some useless pacemaker leads are left in patients when a pacemaker is removed and replaced. On the other hand, life-threatening complications can require the removal of a pacemaker lead from the vein of a patient. For example, if a pacemaker lead becomes infected, septicemia and endocarditis can result; if there are too many leads positioned in a vein, the vein can be obliterated; if multiple incompatible leads are positioned in the same vein, they can interfere with the pacing function; and if a lead migrates, mechanically induced ventricular arrhythmias can occur. Furthermore, it is beneficial to remove a lead from a patient when removing and replacing a pacemaker due to the risk of undetected lead thrombosis which can result in stroke, heart attack, or pulmonary embolism.

Pacemaker leads are typically removed from the vein of a patient using a dilator sheath. Commonly, two coaxial dilator sheaths are positioned over the lead and advanced therealong for loosening the lead from the fibrotic tissue on the vein wall. Some dilator sheaths are formed from plastic tubes, which are flexible for bending around the natural anatomical curvatures of the vascular system. A problem with the plastic dilator sheaths is that the leading edge of the dilator sheath is weak and can lose its edge and buckle onto the lead during use. As a result, the plastic dilator sheath is damaged and unusable before the lead is loosened from the fibrotic tissue. Furthermore, flexible plastic sheaths commonly kink when subjected to tough fibrotic tissue. This problem is further heightened when the sheath is bent around a vessel curve. Other dilator sheaths are formed from metal tubes, which include a sharp leading edge for encountering fibrotic tissue. A problem with the metallic dilator sheaths is that they are relatively inflexible and resist bending around natural anatomical curvatures. As a result, the metallic dilator sheaths can be difficult or impossible to advance toward the distal end of the pacemaker lead without injuring or obliterating the vein. Plastic sheaths with metal tips are also known; however, kinking problems still exist for the flexible plastic portion as well as there being a concern for the metal tip detaching from the main plastic body.

SUMMARY OF THE INVENTION

The foregoing problems are solved and a technical advance is achieved in an illustrative locally flexible dilator sheath for separating encapsulating tissue from an implanted cardiac electrical lead. In particular, the dilator sheath comprises an elongated tubular member of a rigid material for advantageously separating extremely tough encapsulating tissue from implanted cardiac leads. Advantageously, the rigid tubular member includes a relieved portion which is flexible for laterally bending the sheath around vessel curves in which the cardiac lead is implanted.

The relieved portion of the sheath includes a relief pattern of apertures for providing lateral flexibility of the dilator sheath tube. In the preferred embodiment, the relief pattern apertures advantageously include pairs of diametrically opposed slots that extend radially into the tube. Adjacent pairs of opposed slots are circumferentially offset at a prescribed angle to provide advantageously lateral flexibility in a multitude of directions. The main apertures of the relief pattern are bounded by distal and proximal apertures, which have an aperture area that is less than that of the main apertures. This advantageously provides a gradual change in flexibility from that of the solid tubular member and significantly reduces fracturing of the tubular member when laterally bending the dilator sheath around vessel curves.

In one aspect, the relief apertures include pairs of diametrically opposed slots of which the slots in each pair extend radially into the tube an equal amount and are separated from each other a prescribed distance. In addition, adjacent pairs are longitudinally spaced a uniform distance apart in addition to being circumferentially offset to add uniform lateral flexibility to the sheath. The distal and proximal slots extend into the tube to a lesser depth to again provide a gradual transition in lateral flexibility.

To enhance the safety of the dilator sheath, a coating material such as a tube is positioned or, preferably, heat shrunk over the relief apertures to provide continuity to the dilator sheath should the rigid material of the sheath fracture. Furthermore, the heat shrink tubing advantageously prevents separated tissue from entering into the passage of the dilator sheath, thereby preventing advancement of the sheath over the implanted and encapsulated lead.

In another aspect, the relief pattern can include a plurality of various-shaped apertures such as rectangular, round, square, elliptical, teardrop, or a combination thereof. Furthermore, the relief pattern can include a plurality of unopposed apertures positioned in the relieved portion of the tubular member. The various-shaped apertures advantageously provide various flexibility combinations for the dilator sheath to meet specific medical applications.

Preferably, the rigid material includes a stainless steel material, but alternatively or in combination can include at least one from a group consisting of titanium, nitinol, nickel-based alloys, and a reinforced liquid crystal polymer. The shrink tube is formed preferably from a polyester or a polyamide, but can also include a polytetrafluoroethylene tube that is fitted over the outer surface of the rigid tubular member.

BRIEF DESCRIPTION OF THE DRAWING

FIGS. 6–8 depict different shaped apertures that can be utilized in the relieved portion of the dilator sheath of FIG. 1;

FIGS. 9–11 represent various positions of relief apertures in alternative embodiments of the dilator sheath of FIG. 1; and FIG. 12 depicts an enlarged partially sectioned view of the beveled distal cutting end of the dilator sheath of FIG. 1.

DETAILED DESCRIPTION

Figure 1:
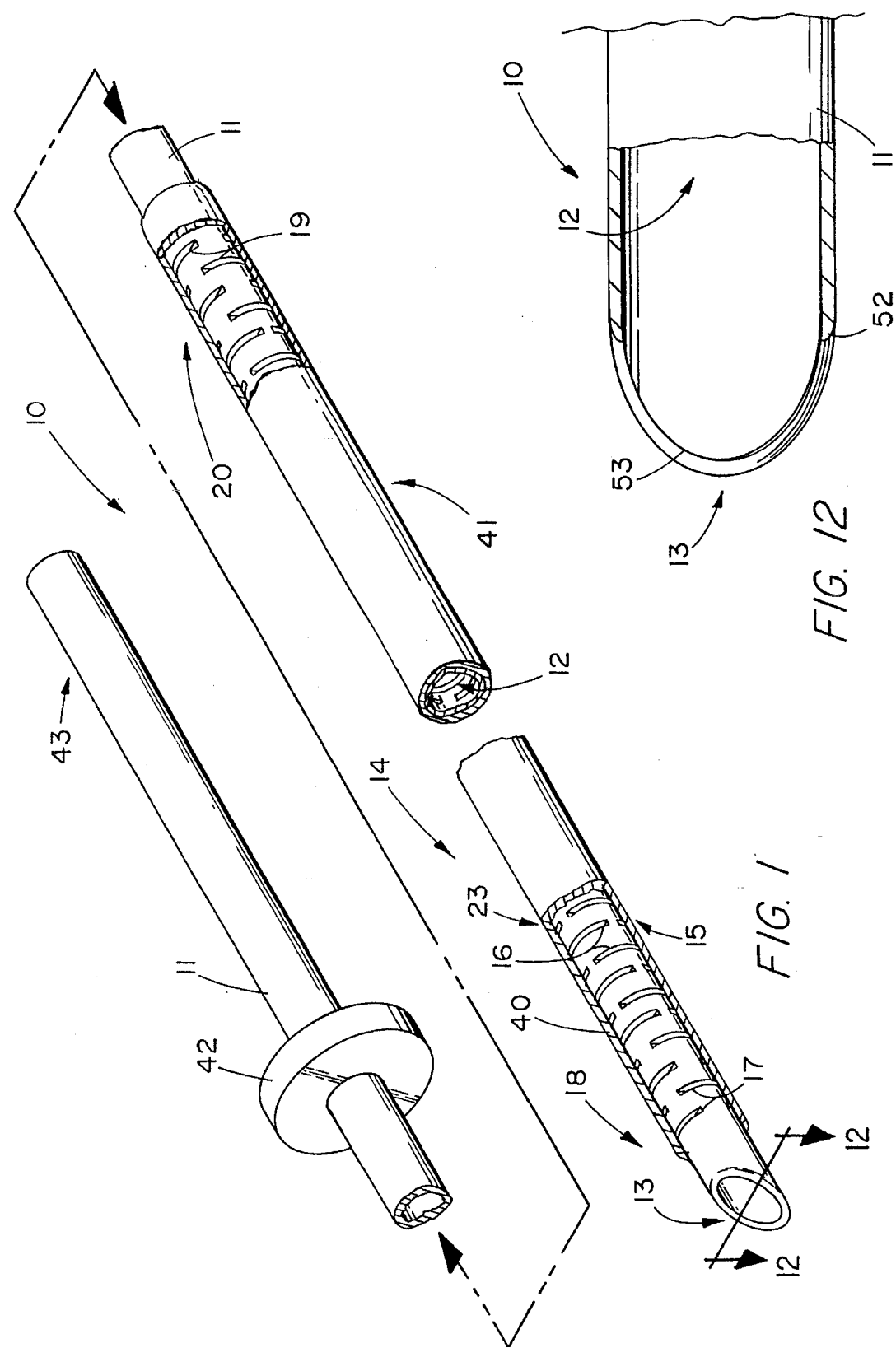
FIG. 1 depicts a preferred embodiment of an illustrative locally flexible dilator sheath for separating encapsulating tissue from an implanted cardiac electrical lead.

FIG. 1 depicts a preferred embodiment of an illustrative locally flexible dilator sheath 10 for separating encapsulating tissue from an implanted cardiac electrical lead. The dilator sheath comprises an elongated tubular member 11 with passage 12 extending longitudinally therethrough. The passage is sized for placement of the elongated tubular member over a cardiac electrical lead, such as from an pacemaker or defibrillator, that is implanted in a patient's vessel extending to or from the heart. The tubular member is of a rigid material such as stainless steel with a beveled distal cutting end 13 for separating extremely tough encapsulating tissue from the implanted lead. The tubular member includes a relieved portion 14 that provides local flexibility to the sheath for laterally bending around vessel curves in which the lead is implanted. Circular disk-shaped flange 42 is positioned near proximal end 43 of the tubular member. As a result, an attending physician can readily push the dilator sheath over the lead and separate extremely tough encapsulating tissue from the implanted lead. Relieved portion 14 includes relief apertures 23 that are formed in the tubular member to relieve the stresses formed in the rigid tubular member when laterally bent around vessel curves. Without such relief, the rigid tubular member could readily sever the implanted lead or perforate the vessel wall. Furthermore, the rigid tubular member could also kink or fracture in the patient's vessel, which could easily require another more invasive surgical procedure to remove the kinked sheath or fractured pieces thereof.

As a measure of safety, coating material 40 is applied over relieved portion 14 to maintain structural integrity of the dilator sheath. Preferably, the coating material comprises a polyester tube 41, that is heat shrunk over and into the apertures of the relief pattern to ensure that the rigid tubular member when fractured can be readily withdrawn from the patient's vessel without the need for a more invasive surgical procedure. Heat shrink tubing is commercially available and includes a variety of polyamides in addition to the polyester. Furthermore, a polytetrafluoroethylene tube can be inserted over the rigid tubular member to provide a lubricious outer surface to enhance the ease in which the dilator sheath passes through the encapsulated tissue. In addition, heat shrunk tube 41 prevents separated tissue from passing through the apertures of the relief pattern and into passage 12 of the elongated member tube. Presence of separated tissue in the tube could bind the separated lead in the passage of the tube, thereby making the lead removal procedure more difficult.

Relief apertures 23 include main apertures 16 bounded by distal apertures 17 proximate distal end 18 and proximal apertures 19 proximate proximal end 20. As depicted, the relief apertures include pairs of diametrically opposed slots. Adjacent pairs of the slots are circumferentially offset at approximately a 90 degree angle to provide lateral flexibility in at least four different directions. Opposing slots in each pair of the main aperture slots are laterally separated a minimum prescribed distance to provide maximum lateral flexibility and to maintain longitudinal integrity of the tubular member. Adjacent pairs of opposed slots of the main aperture slots are longitudinally spaced a prescribed distance apart to also enhance lateral flexibility while also maintaining longitudinal integrity of the tubular member. Opposing slots in each pair of the distal and proximal aperture slots are laterally separated a greater distance from each other than that of the main aperture slots so as to provide a gradual transition in flexibility from the solid rigid tube at the proximal and distal ends thereof to the main aperture slots.

Figure 2:
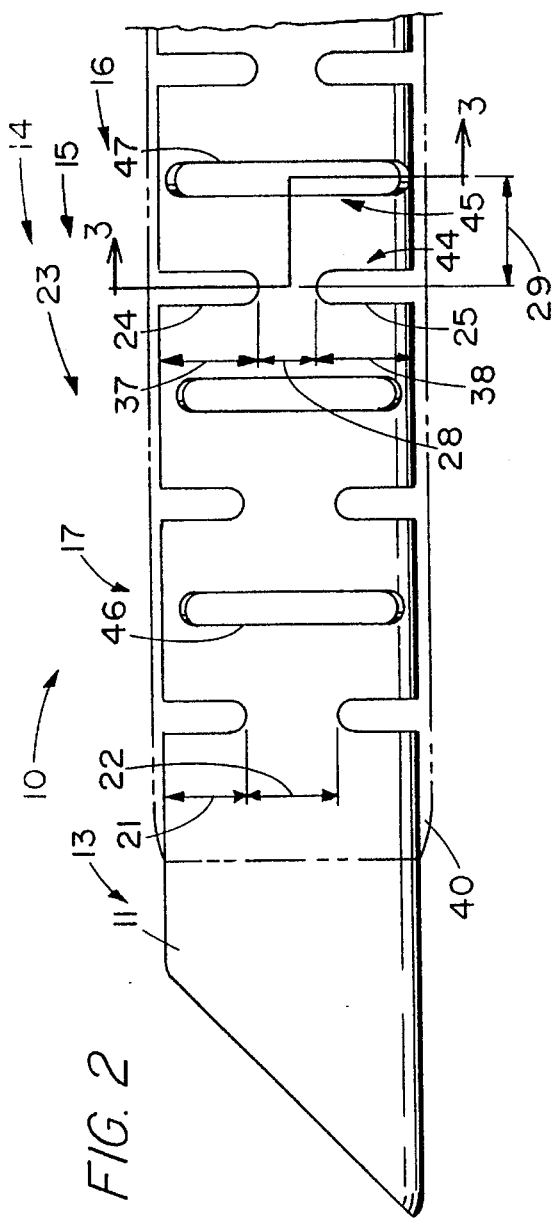
FIG. 2 depicts an enlarged partial view of the relieved portion proximate the distal end of the locally flexible dilator sheath of FIG. 1.

FIG. 2 depicts an enlarged partial view of relieved portion 14 proximate distal end 13 of locally flexible dilator sheath 10 of FIG. 1. Diametrically opposed slots 24 and 25 of pair 44 extend perpendicularly into rigid tubular member 11 to respective depths 37 and 38 with resulting separation distance 28 therebetween. Although opposing slots 24 and 25 are preferably equal in depth to provide equal flexibility in opposing directions, depths 37 and 38 of opposing slots 24 and 25 can be different to provide unequal flexibility in opposing directions. Furthermore, the spacing between the opposing slots in the pairs can also be varied to vary the lateral flexibility of the tubular member along its length.

By way of example, tubular member 11 is a stainless steel tube approximately 15" in length with an outside diameter of approximately 0.156" and an inside diameter of approximately 0.136", thereby resulting in a wall thickness of approximately 0.010". Alternatively, the rigid material of the elongated tubular member can be any one or more materials from a group consisting of titanium, nitinol, nickel-based alloys, and reinforced plastics. Reinforced plastics are increasingly being used as replacements for metal in surgical tools. Reinforced plastics include commercially available reinforced liquid crystal polymers including carbon- or glass-filled formulations. Reinforced liquid crystal polymers are, for example, available from the Hoechst Celanese Corporation under the VECTRA tradename. Main aperture slots 16 extend longitudinally along the length of the tube for approximately 9.30" approximately 0.55" from the far most end of beveled distal cutting end 13. Main aperture slots are each approximately 0.020" wide, rounded at the bottom thereof, and extend perpendicularly into tube 11 to a maximum depth of approximately 0.060" with approximately 0.036" radial separation distance 28 apart. Adjacent pairs 44 and 45 of the main aperture slots are longitudinally spaced a prescribed distance 29 apart of approximately 0.060". This distance, commonly referred to as pitch, is a centerline-to-centerline distance, whereas the actual distance between adjacent slots is approximately 0.040".

Opposing slots of distal and proximal aperture slots 17 and 19 are identical to those of main aperture slots 16, except that they extend perpendicularly into tube 11 to a maximum depth 21 of approximately 0.050" with a 0.056" radial separation distance 22 apart. As a result, distal and proximal aperture slots 17 and 19 have an aperture area 46 less than main aperture area 47. Preferably four pairs of opposing slots are each included in distal and proximal apertures 17 and 19. As a result, the lesser depth of distal and proximal aperture slots provides a gradual transition in flexibility from the rigid tube ends to the main aperture slots of the relief pattern.

Figure 3:
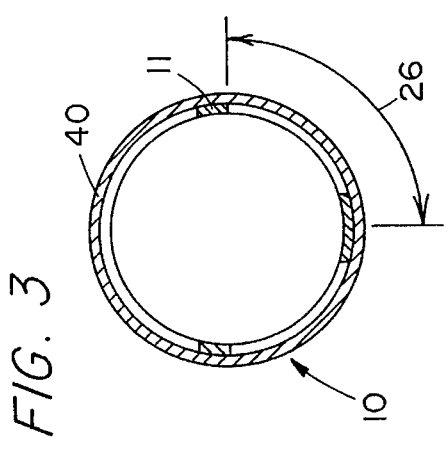
FIG. 3 depicts a cross-sectional view of the tubular member of FIG. 2 taken along the line 3—3.

FIG. 3 depicts a cross-sectional view of tubular member 11 of FIG. 2 taken along the line 3—3. This offset line taken through the midpoint of the material separating diametrically opposed slots of adjacent pairs 44 and 45 illustrates an offset angle 26 of approximately 90 degrees.

Figure 4:
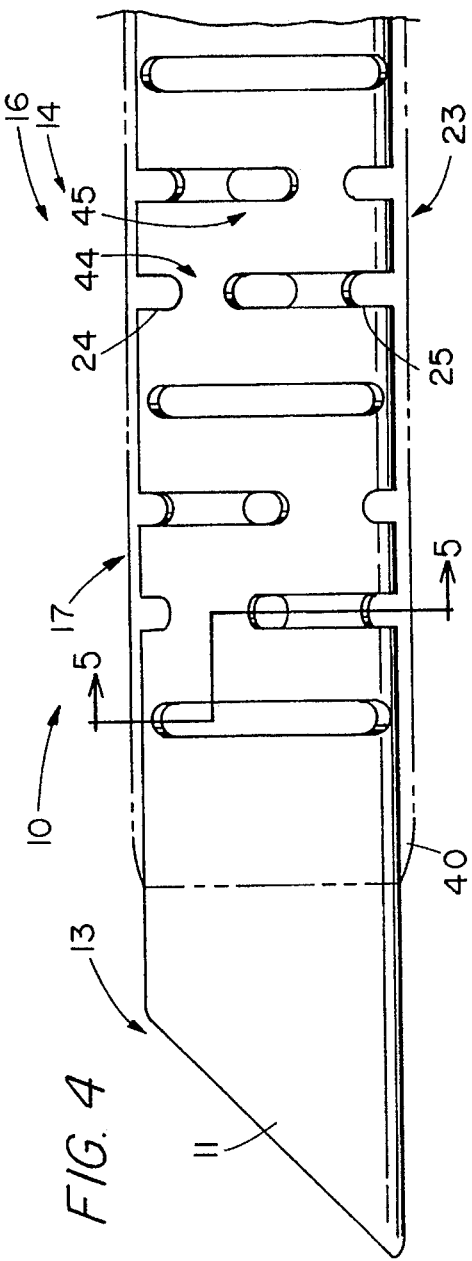
FIG. 4 depicts an enlarged partial view of the relieved portion proximate the distal end of another embodiment of the locally flexible dilator sheath of FIG. 1.

FIG. 4 depicts an enlarged partial view of relieved portion 14 proximate distal end 13 of another embodiment of locally flexible dilator sheath 10 of FIG. 1. In this embodiment, adjacent pairs 44 and 45 of diametrically opposed slots have an offset angle 27 of approximately 60 degrees. As a result, the material of the tube separating each pair of diametrically opposed slots helically spirals around the longitudinal axis of tube 11. This provides flexibility of the dilator sheath in additional lateral directions.

Figure 5:
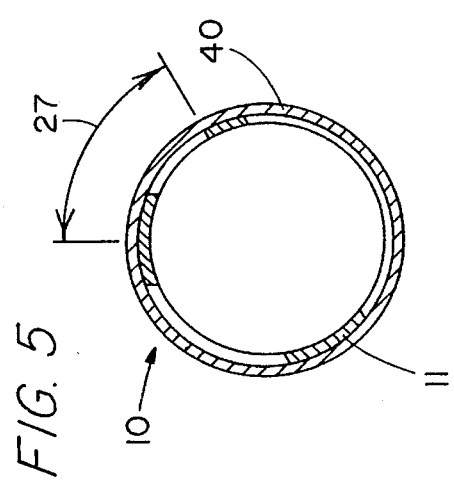
FIG. 5 depicts a cross-sectional view of the dilator sheath of FIG. 4 taken along the line 5—5.

FIG. 5 depicts a cross-sectional view of the dilator sheath of FIG. 4 taken along the line 5—5. This cross-sectional view further illustrates that adjacent pairs of diametrically opposed slots have an offset angle 27 of approximately 60 degrees.

Figure 7:
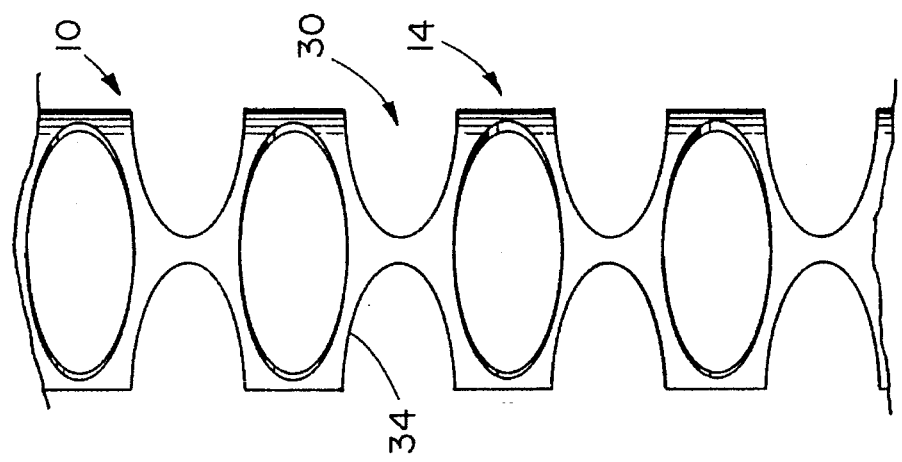
Figure 6:
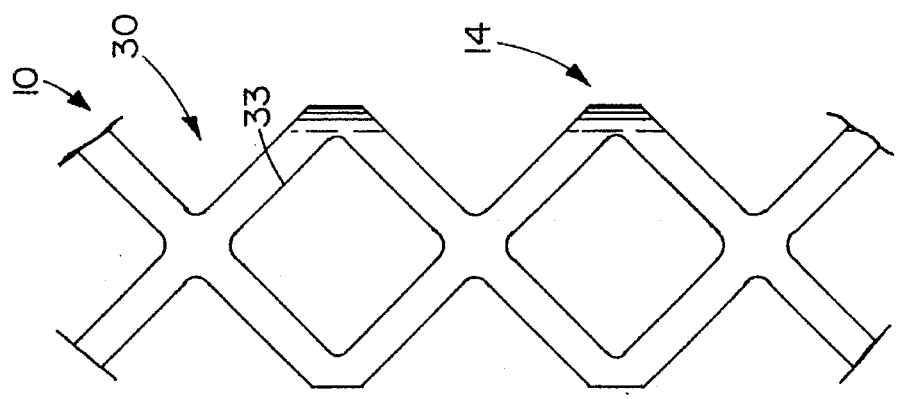

FIGS. 6–8 depict a plurality 30 of different shaped apertures that can be utilized in relieved portion 14 of dilator sheath 10 of FIG. 1. FIG. 6 depicts a plurality 30 of diametrically opposed square-shaped apertures 33. Adjacent pairs of square-shaped apertures are circumferentially offset at an angle of approximately 90 degrees. Similarly, FIG. 7 depicts a plurality 30 of diametrically opposed elliptically shaped apertures 34. FIG. 8 depicts a plurality of various-shaped apertures 31–36, which include rectangular-shaped aperture 31, round-shaped aperture 32, teardrop-shaped aperture 35 along with apertures 36, 48, and 49, which represent combinations of the aforementioned shaped apertures.

Figure 9:
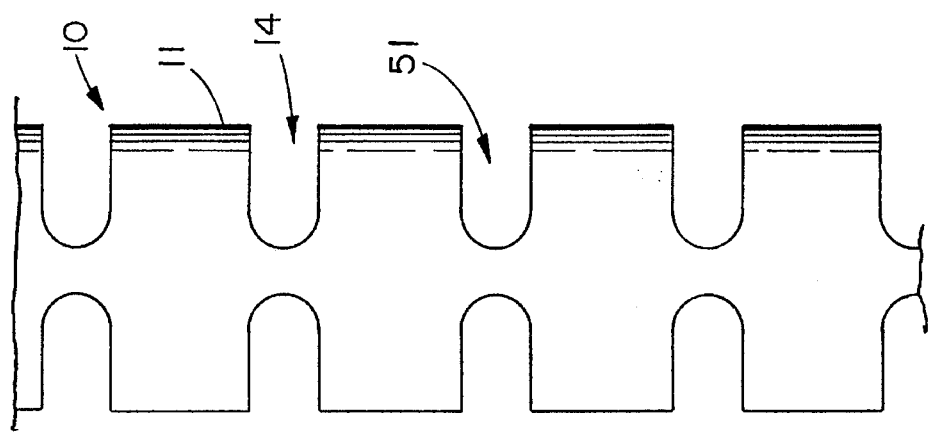

FIGS. 9–11 represent various positions of apertures 39, 50, and 51 in relieved portion 14 in alternative embodiments of dilator sheath 10 of FIG. 1. FIG. 9 depicts pairs of diametrically opposed slots 51 extending perpendicularly into tube 11 without any circumferential offset between adjacent pairs. FIG. 10 depicts unopposed slots 39 extending perpendicularly into tube 11 from only one direction. FIG. 11 depicts unopposed slots 50 extending perpendicularly into tube 11 alternating from two opposed directions. The positioning of apertures in the relieved portion of the dilator sheath tube allows for various degrees of lateral flexibility in selected directions as the particular medical application requires.

FIG. 12 depicts an enlarged partially sectioned view of beveled distal cutting end 13 of dilator sheath 10 of FIG. 1. The beveled distal cutting end is rounded to form annularly closing outside surface 52. This advantageously prevents inadvertent cutting of attending personnel. However, cutting edge 53 of the beveled distal cutting end presents a sharp edge for separating encapsulating tissue from the implanted cardiac lead.

It is to be understood that the above-described locally flexible dilator sheath is merely an illustrative embodiment of the principles of this invention and that other dilator sheaths may be devised by those skilled in the art without departing from the spirit and scope of this invention. In addition, the dilator sheath with relief apertures therein may be capped at the distal end thereof and used in combination with suction for removing plaque from the walls of the vascular system. In addition, a pull wire can be passed through the elongated tubular member and attached to the distal tip thereof. By pulling on the wire, the tube can be laterally deflected. Better directional control can be obtained by slotting the tube in one direction only as depicted in the aforementioned figures. When the orientation of the slotted pairs helically spirals along the length of the tube as depicted in FIGS. 4 and 5, the tube will deflect into a helical spiral or corkscrew when the pull wire is actuated. This has several vascular system applications. One, the spiralling mechanism can be used as a means to anchor a catheter to a blood vessel. Two, by using the spiralling mechanism in an electrophysiology catheter with a plurality of electrodes, the helical spiral can map a large area of the ventricle or atrium at a given time. The helical spiral can also maintain the position of the catheter by expanding against the wall of the heart chamber. Thirdly, the spiralling mechanism can expand against a blood vessel wall to enhance the removal of plaque from vascular system walls. As previously suggested, the apertures of the relieved portion of the dilator need not be symmetrical about the longitudinal axis of the tube. By adjusting the depth of the relieved portion apertures along the length of the tube and/or by varying the distance between the apertures or slots along the length of the tube, various curves or shapes can be formed when the tube is deflected by either an external force or by an internal force such as that exerted by a pull wire. It is further contemplated that the relieved portion of the rigid tube can be formed by etching or removing portions of the wall thickness either singly or in combination with apertures that extend entirely through the tube wall.

What is claimed is:

1. A locally flexible dilator sheath (10) comprising:
an elongated tubular member (11) of a rigid material having a passage (12) extending longitudinally therethrough and sized for placement of said elongated tubular member over a cardiac electrical lead that is implanted in a vessel, a distal end (13) shaped for separation of encapsulating tissue from an implanted lead, and a relieved portion (14), whereby said relieved portion is flexible for laterally bending around vessel curves in which a cardiac electrical lead is implanted.

2. The dilator sheath of claim 1 wherein said relieved portion (14) includes a relief pattern (15) formed in said elongated tubular member.

3. The dilator sheath of claim 2 wherein said relief pattern includes a plurality of relief apertures (23) positioned in said elongated tubular member.

4. The dilator sheath of claim 2 wherein said relief pattern includes a plurality of main apertures (16), a plurality of distal apertures (17) proximate a distal end (18) of said relief pattern, and a plurality of proximal apertures (19) proximate a proximal end (20) of said relief pattern.

5. The dilator sheath of claim 4 wherein said distal and said proximal apertures have an aperture area (46) less than a main aperture area (47) of said main apertures.

6. The dilator sheath of claim 2 wherein said relief pattern includes pairs of diametrically opposed slots (24,25).

7. The dilator sheath of claim 6 wherein adjacent pairs (44, 45) of said pairs of diametrically opposed slots are circumferentially offset a prescribed angle (26,27).

8. The dilator sheath of claim 6 wherein slots in a pair (44) of said pairs of diametrically opposed slots are laterally separated from each other a prescribed distance (28).

9. The dilator sheath of claim 6 wherein adjacent pairs of said pairs of diametrically opposed slots are longitudinally spaced a prescribed distance (29) apart.

10. The dilator sheath of claim 6 wherein a first slot (24) in a pair (44) of said pairs of diametrically opposed slots extends into said tubular member a first depth (37).

11. The dilator sheath of claim 10 wherein a second slot (25) in said pair (44) of said pairs of diametrically opposed slots extends into said tubular member a second depth (38).

12. The dilator sheath of claim 1 wherein said relieved portion includes a plurality (30) of at least one of rectangular (31), round (32), square (33), elliptical (34), and teardrop-shaped (35) apertures or a combination (36) thereof.

13. The dilator sheath of claim 1 wherein said relieved portion includes a plurality of unopposed apertures (39) positioned in said relieved portion of said tubular member.

14. The dilator sheath of claim 1 further comprising a coating (40) extending over said relieved portion.

15. The dilator sheath of claim 14 wherein said coating includes a plastic tube (41).

16. The dilator sheath of claim 15 wherein said plastic tube comprises at least one from a group consisting of polytetrafluoroethylene, polyamides, and polyester.

17. The dilator sheath of claim 1 wherein said rigid material includes at least one from a group consisting of stainless steel, titanium, nitinol, nickel-based alloys, and a reinforced liquid crystal polymer.

18. A locally flexible dilator sheath (10) comprising:

an elongated tubular member (11) of a rigid material having a passage (12) extending longitudinally therethrough and sized for placement of said elongated tubular member over a cardiac electrical lead implanted in a vessel, a distal end (13) shaped for separation of encapsulating tissue from an implanted lead, and a relieved portion (14) having a relief pattern (15) formed therein; and a flexible plastic coating material (40) positioned over said relieved portion of said elongated tubular member, whereby said relieved portion is flexible for laterally bending around vessel curves in which a cardiac electrical lead is implanted.

19. The dilator sheath of claim 18 wherein said relief pattern includes pairs of diametrically opposed slots (24,25), adjacent pairs (44,45) of said pairs of said diametrically opposed slots being circumferentially offset a prescribed angle (26,27).

20. A locally flexible dilator sheath (10) comprising:

an elongated tubular member (11) of a rigid stainless steel material having a passage (12) extending longitudinally therethrough and sized for placement of said elongated tubular member over a cardiac electrical lead implanted in a vessel, a distal end (13) beveled and shaped for separation of encapsulating tissue from an implanted lead, and a relieved portion (14) having a relief pattern (15) of main pairs (16) of diametrically opposed slots (24,25) formed therein, adjacent pairs (44,45) of said diametrically opposed slots being longitudinally spaced a prescribed distance apart (29) and circumferentially offset a 90° angle (26), slots of said pairs of diametrically opposed slots being laterally separated from each other a first separation distance (28), said relief pattern also having distal pairs (17) and proximal pairs (19) of diametrically opposed slots, each pair of slots being laterally separated from each other a second separation distance (22) greater than said first separation distance;

a tube (41) of polyester material heat shrunk over said relieved portion including said relief pattern of said elongated tubular member; and a flange (42) positioned proximal said relieved portion on said elongated tubular member, whereby said relieved portion is flexible for laterally bending around vessel curves in which a cardiac electrical lead is implanted.

\* \* \* \* \*